United States Patent [19]

Ohlsson et al.

[11] 4,437,538
[45] Mar. 20, 1984

[54] EAR-CAP

[76] Inventors: Ingemar Ohlsson, Katarinavägen 18, Stockholm, Sweden, S-116 45; Sten J. L. Wolf, Dånviksvägen 1, Rönninge, Sweden, S-144 00

[21] Appl. No.: 363,460
[22] Filed: Mar. 30, 1982
[51] Int. Cl.³ .................. A61F 11/02; H04R 25/00
[52] U.S. Cl. .................................... 181/129; 128/152
[58] Field of Search ................ 181/129; 128/152; 179/182 R, 182 A

[56] References Cited

U.S. PATENT DOCUMENTS 1,305,828  6/1919  Miller .............................. 128/152
3,798,393  3/1974  Gorike ............................ 179/182 R Primary Examiner—Benjamin R. Fuller
Attorney, Agent, or Firm—Holman & Stern

[57] ABSTRACT

This invention concerns an ear protecting means and specially an ear-cap which protects the ear against dangerous noise. The object of the invention is to silence the dangerous noise while permitting talking communication between two persons. The invention consists of an ear-cap, which is placed against the exterior of an ear, and which includes a cushion which covers the ear and is of elastic and porous material, which transmits sound, the outside of said cushion being at least to its main part covered by a perforated disc, said disc defines a cavity which is closed beside the perforations, the thickness of said disc, the amount of perforations and their size and the volume of the cavity being adapted to the requested property of absorption of sound of a certain range of frequency.

9 Claims, 2 Drawing Figures

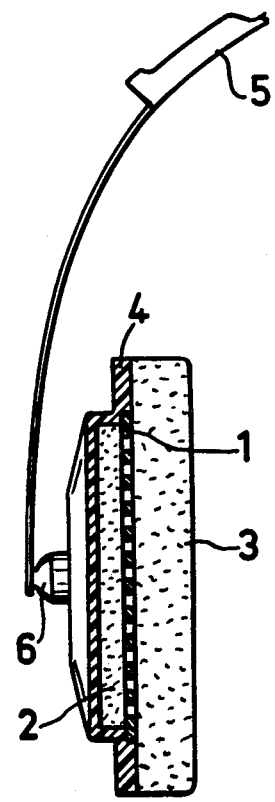
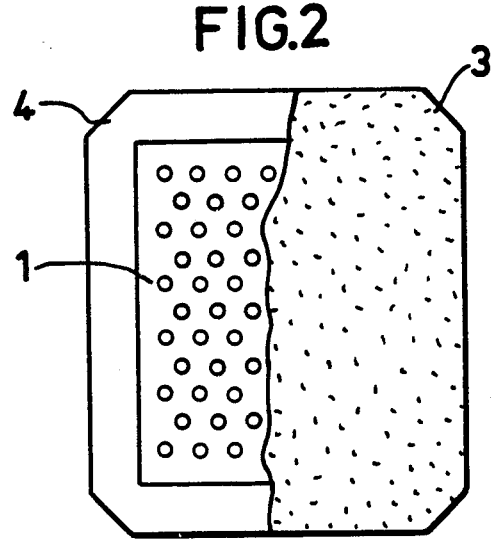

EAR-CAP

This invention concerns an ear protecting means and specially an ear-cap which protects the ear against dangerous noise.

The invention is specially useful for dentists and it has been found that the sound level of a dental drilling equipment is over 83 dB within the frequency range of 4-6 kHz. This sound level is about 2 dB too high to be acceptable.

The main object of the invention is to silence the dangerous noise while permitting talking communication between the dentist and his assistant or the nurse. The protecting means should also be light and easy to wear.

The invention consists of an ear-cap, which is placed against the exterior of an ear. It is characterized in that said ear-cap includes a cushion which covers the ear and is of elastic and porous material, which transmits sound, the outside of said cushion being at least to its main part covered by a perforated disc, which defines a cavity which is closed beside the perforations, the thickness of said disc, the amount of perforations and their size and the volume of the cavity being adapted to the requested property of absorption of sound of a certain range of frequency.

BRIEF DESCRIPTION OF THE DRAWING

An embodiment of the invention will now be described with reference to the attached figures.

FIG. 1 thereby is a cross-section through the left part of a head set of ear-caps according to the invention.

FIG. 2 is the ear-cap according to FIG. 1 seen from the right side.

DETAILED DESCRIPTION OF THE DRAWING

The shown sound protecting means is formed to absorb sound of octavos around 5 KHz and is formed as an acoustic band-rejecting filter. The absorbing means is in the form of an Helmholz-resonant means, consisting of perforated plastic disc 1 of a certain thickness covering a cavity 2.

In order to reduce the Q-valve of the absorbent the cavity 2 is filled with an absorbing material as foamed plastic.

Between the plastic disc 1 and the ear is a cusion 3 of foamed plastic. The material of the cushion is choosen according to proper porosity and elasticity. This is of importance because an ear-cap, which does not rest perfectly against the ear, does not work properly. The perforations of the disc 1, the thickness of the disc and the distance to the bottom of the cavity 2 are so dimensioned, that the middle frequence of the absorbent will be 5 KHz. The earcap further includes an earcap housing 4 having a recessed portion therewithin partially defining a sound deadening cavity.

The ear-cap is suspended by a clip, the left parts of which are shown in FIG. 1. The ear-cap is fastened to the clip by a ball joint 6.

The invention is not restricted for the use to absorb the sound of dentists drilling equipment. It can also be used in other environments for absorbing noise within the same range of frequency as mentioned above. The invention can also be modified for other frequencies.

We claim:

1. Ear protecting means for protecting the auditory canal of the ear from sound vibrations within a predetermined frequency range comprising:

an earcap including sound absorbing means for absorbing sound of said predetermined frequency and sound transmitting means for transmitting ambiant sount vibrations to said auditory canal and to said sound absorbing means, a housing for said earcap having a recessed portion therewithin, said sound absorbing means comprising a sound-damping cavity within said earcap for damping sound of said predetermined frequency, said cavity being defined by the recessed portion of said housing and a perforated disc element having perforations adapted for admitting sound of said predetermined frequency to said cavity for damping therewithin; and said sound transmitting means comprising an ear cushion of sound-transmitting material having an inner surface adapted to bear on the outer auditory canal of the ear and an outer surface disposed against the perforated portion of said perforated disc element so that sound vibrations entering the auditory canal must first pass through said cushion of sound transmitting material and so that sound vibrations of said predetermined frequency passing through said cushion also pass through said perforated disc element into said cavity for damping therewithin.

2. The invention of claim 1, wherein a sound-absorbent material is disposed in said sound-damping cavity.

3. The invention of claim 2, wherein said sound-absorbent material is a foamed plastic.

4. The invention of claim 1, wherein said cushion of sound-transmitting material is a cushion of foamed plastic.

5. The invention of claim 4, wherein said sound-absorbing means is adapted to absorb sound in a frequency range of 4 to 6 kHz.

6. The invention of claim 1, wherein the ear protection means is adapted to protect the auditory canal of the ear from sound of a frequency emanating from dental drilling equipment.

7. The invention of claim 1, wherein the sound-absorbing characteristics of the sound-absorbing means are determined by the volume of the sound-damping cavity, the thickness of the perforated disc element, and the number and size of the perforations in the disc element.

8. The invention of claim 1, wherein the earcap further includes retaining means for retaining the ear cushion against the ear.

9. The invention of claim 1, wherein the ear protecting means further comprises two earcaps and biasing means for biasing each of the earcaps against an ear.

* * * * *